United States Patent [19]

Zaiger

[11] Plant 4,304

[45] Sep. 19, 1978

[54] ALMOND TREE

[76] Inventor: Chris Floyd Zaiger, 537 Rosemore Ave., Modesto, Calif. 95351

[21] Appl. No.: 831,099

[22] Filed: Sep. 6, 1977

[51] Int. Cl.[2] ..... A01H 5/03

[52] U.S. Cl. ..... Plt./30

[58] Field of Search ..... Plt./30

*Primary Examiner*—Robert E. Bagwill

[57] ABSTRACT

A new variety of almond tree with upright, stocky growth of medium vigor and size. The tree is further characterized by having heavy foliage of medium size leaves, an abundance of heavy white bloom, and being a regular and heavy bearer of medium size, sweet kernel almonds. The blooming time being after Nonpareil Almond (unpatented) but just ahead of Mission Almond (unpatented) and the harvest time being early, essentially with Nonpareil Almond.

1 Drawing Figure

ORIGIN OF THE VARIETY

The herein variety of almond tree was originated by me in my experimental orchard located near Modesto, Calif., from a second generation seedling of a cross between two self fertile peach almonds. A selection having desirable characteristics, including self fertility, was made from the first generation and this selection was selfed to give a large number of seedlings from which this new and distinct variety of self fertile almond was selected.

ASEXUAL REPRODUCTION OF THE VARIETY

The present variety was asexually propagated by budding, as performed near Modesto, Calif., shows that the said characteristics come true to form and are established and transmitted through succeeding propagation.

SUMMARY OF THE VARIETY

The present variety of almond tree is of medium size and vigor, the growth being upright and stocky and a regular and heavy bearer of medium size nuts which are easy to harvest and hull. The blooming period being after Nonpareil Almond but slightly before Mission Almond and the harvest time being early, essentially with Nonpariel. The medium size kernels in most cases are completely sealed by a soft shell, having a relatively high percentage of kernel to shell. The present variety of almond tree is further characterized by being self fruitful and also having the ability to serve as an effective pollenizer for other varieties of almonds.

BRIEF DESCRIPTION OF THE PHOTOGRAPHS

The drawing is a photographic reproduction in color illustrating twigs with a cluster of nuts attached; nuts in the hull, nuts out of hull but in the shell, and kernels out of the shell. The photographs also show typical specimens of foliage with upper and lower surfaces of the leaves being illustrated.

DESCRIPTION OF THE VARIETY

The botanical details of this new and distinct variety of almond tree, as based upon observations of specimens grown at Modesto, Calif., with color terminology in accordance with Reinhold Color Atlas by A. Kornerup and J. H. Wanscher.

Tree:
- *Size.*—Medium.
- *Vigor.*—Medium.
- *Density.*—Dense.

Trunk:
- *Form.*—Stocky.
- *Texture.*—Medium.

Branches:
- *Form.*—Stocky.
- *Texture.*—Medium.
- *Lenticels.*—Medium number and size.
- *Branching habit.*—Medium upright.

Foliage: Abundant.

Leaves:
- *Size.*—Small. Average length — 2¾". Average width—¾".
- *Shape.*—Ovate.
- *Thickness.*—Medium.
- *Texture.*—Smooth.
- *Margin.*—Crenate.
- *Petiole.*—Medium length. Medium thickness.
- *Color.*—Upper surface — grayish green (28-E-6 to 28-E-4). Lower surface — dull green (28-E-5 to 28-E-4).
- *Glands.*—Usually two, alternate, positioned mainly on petiole, sometimes on base of blade.

Bloom:
- *Amount.*—Heavy.
- *Color.*—White.
- *Blooming period.*—Usually 2 to 3 days before Mission.

Crop:
- *Bearing.*—Regular bearer.
- *Productivity.*—Very heavy.
- *Distribution of nuts on tree.*—Well distributed.
- *Harvest period.*—Approximately with Nonpareil.

Hull:
- *Outer surface.*—Relatively smooth.
- *Suture.*—Lightly ridged.
- *Dehiscence.*—Opens freely.
- *Splitting.*—Along suture.

Nut:
- *Size.*—Average length 1¼". Average width ⅝".
- *Form.*—Length/width — ovate. Width/thickness — plump to medium.

*Shell.*—Soft.
*Color.*—Brownish orange (5-C-6).
*Pits.*—Small, numerous.
*Base.*—Square to ventrally oblique.
*Stem scar.*—Small to medium.
*Apex.*—Acute.
*Inter surface.*—Medium color.
*Wing.*—Broad and thin.
*Percentage of kernel to nut.*—Averages approximately 63%.

Kernel:
*Size.*—Average length 7/8". Average width 7/16".
*Form.*—Length/width — ovate. Width/thickness — plump to medium.
*Base.*—Round.
*Apex.*—Obtuse. Acuminate. Slightly prolonged at tip.
*Texture.*—Smooth to wrinkled.
*Pellicle.*—Thin.
*Number of doubles.*—Medium.
*Flavor.*—Sweet.
*Quality.*—Good.
*Color of skin.*—Golden yellow (5-B-7).
*Color of meat.*—White (1-A-1).

The tree and its nuts herein described may vary in slight detail due to climatic and soil conditions under which it may be grown. The description is that of the variety produced under the ecological conditions prevailing at Modesto, Calif., and the characteristics are found to hold true in asexual reproduction of the variety.

I claim:

1. A new and distinct variety of almond tree, as shown and described, characterized by the tree being of medium size and vigor, medium upright in growth, having a heavy set of bloom, blooming a few days before Mission, and a heavy and regular bearer of medium size nuts, which are well distributed along the branches and are easy to harvest and hull; the variety being self-fertile and harvesting with Nonpareil.

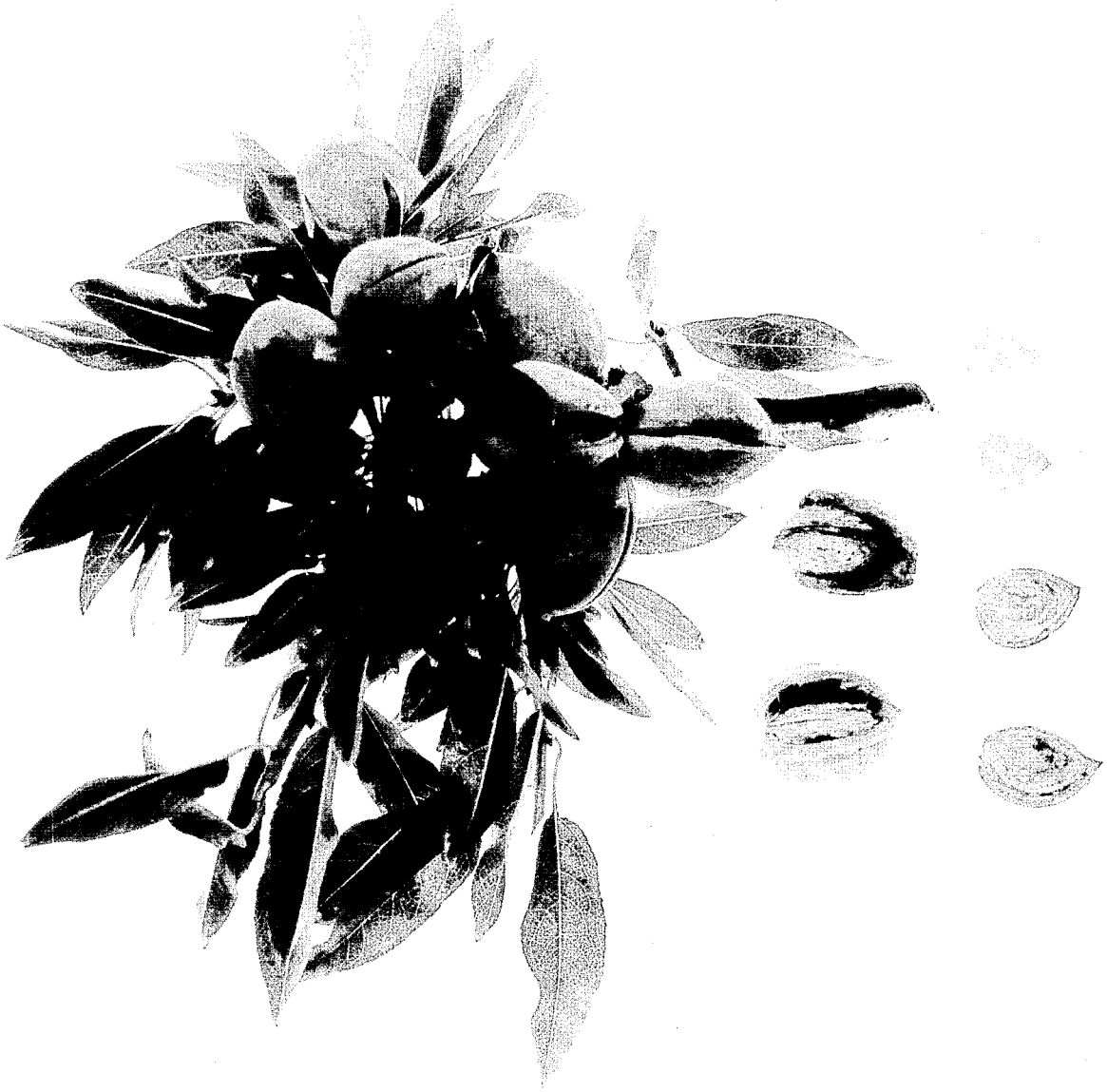

* * * * *